(12) United States Patent
Bøgesø et al.

(10) Patent No.: US 7,351,734 B2
(45) Date of Patent: Apr. 1, 2008

(54) AMINOINDANE DERIVATIVES AS SEROTONIN AND NOREPINEPHRINE UPTAKE INHIBITORS

(75) Inventors: Klaus Peter Bøgesø, Hørsholm (DK); Ask Püschl, Frederiksberg (DK); Jan Kehler, Kgs. Lyngby (DK); Peter Bregnedal, Allerød (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 465 days.

(21) Appl. No.: 10/496,730

(22) PCT Filed: Dec. 18, 2002

(86) PCT No.: PCT/DK02/00873

§ 371 (c)(1), (2), (4) Date: Nov. 19, 2004

(87) PCT Pub. No.: WO03/055873

PCT Pub. Date: Jul. 10, 2003

(65) Prior Publication Data

US 2005/0085530 A1 Apr. 21, 2005

Related U.S. Application Data

(60) Provisional application No. 60/343,360, filed on Dec. 21, 2001.

(30) Foreign Application Priority Data

Dec. 21, 2001 (DK) ............... 2001 01939

(51) Int. Cl.
- *A61K 31/28* (2006.01)
- *C07D 321/00* (2006.01)
- *C07D 307/00* (2006.01)

(52) U.S. Cl. .............. 514/430; 549/200; 549/429
(58) Field of Classification Search ........... 564/305; 514/579

See application file for complete search history.

(56) References Cited

U.S. PATENT DOCUMENTS

| | | | |
|---|---|---|---|
| 4,873,344 A * | 10/1989 | Bogeso et al. | 549/77 |
| 5,559,134 A | 9/1996 | Buchmann et al. | |
| 5,773,463 A * | 6/1998 | Harling et al. | 514/473 |

FOREIGN PATENT DOCUMENTS

| | | |
|---|---|---|
| EP | 0271225 A2 | 6/1988 |
| WO | WO 9210192 A1 | 6/1992 |
| WO | WO 9322293 A1 | 11/1993 |
| WO | WO 9504027 A1 | 2/1995 |
| WO | WO 9504028 A1 | 2/1995 |
| WO | WO 9518617 A1 | 7/1995 |
| WO | WO 95/29907 A1 | 11/1995 |
| WO | WO 96/06840 A1 | 3/1996 |
| WO | WO 9855447 A1 | 12/1998 |
| WO | WO 9935119 A1 | 7/1999 |
| WO | WO 01/10842 A2 | 2/2001 |

OTHER PUBLICATIONS

Clar, E., et al.; "New Benzenogenic Diene Syntheses", Tetrahedron, 1974, vol. 30, p. 3293-3298.
Durani, N., et al.: "Structure-Activity Relationship Of Antiestrogens: A Study Using Triarylbutenone, Benzofuran, And Triarylfuran Analogues As Models For Triarylehtylenes and Triarylpropenones", J. Med. Chem.; 1989; vol. 32, p. 1700-1707.
Ecker, G., et al.; "Structure-Activity Relationship Studies On Benzofuran Analogs Of Propafenone-Type Modulators Of Tumor Cell Multidrug Resistance", J. Med. Chem.; 1996; vol. 39, p. 4767-4774.
Johnston, K. M., et al.: "Friedel-Crafts Cyclisation—IV. Intramolecular VS Intermolecular Acylation with B-Aryl Derivatives Of Propionyl Chloride In Aromatic Substrates", Tetrahedron. 1974, vol. 30, p. 4059-4064.
Klaus P. Bogeso et al.: "3-phenyl-1-indanamines. Potential Antidepressant Activity and Potent Inhibition of Dopamine, Norepinephrine, and Serotonin Uptake", J. Med. Chem., vol. 28, No. 12, 1985, p. 1817-1828.
Smonou, T., et al.: "Convenient Synthetic Sequence For The Preparation Of Indanones", Synthetic Communications, 1990, vol. 20(9), p. 1387-1397.
Sommer, M. B., et al.: "Application of (2-Cyanoaryl)arylacetonitriles In Cyclization And Annulation Reactions. Preparation Of 3-Arylindans, 4-Aryl-3,4-dihydronapthalenes, 4-Arylisoquinolines, 1-Aminonaphthalenes, And Heterocyclic Analogues", J. Org. Chem. 1990, vol. 55, No. 16, pp. 4822-4827.
Zaidlewicz, M., et al.; "Asymmetric Synthesis Of (S)-bufaralol And A Propafenone Analogue", Tetrahedron: Asymmetry, 2003, vol. 14, p. 1659-1664.
Khan, A., et al.: "Venlafaxine in depressed outpatients", Psychopharmacology Bulletin, 1991; vol. 27, No. 2, pp. 141-144.
Wong, D.T.: "Duloxetine (LY 248686): An inhibitor of serotonin and noradrenaline uptake and an antidepressant drug candidate", Exp. Opin. Invest. Drugs, 1998; vol. 7, No. 10, pp. 1691-1699.

* cited by examiner

*Primary Examiner*—Rebecca Anderson
*Assistant Examiner*—Susannah Chung

(57) ABSTRACT

The present invention relates to aminoindane derivatives having the formula I wherein X, Y, U, $R^{1-2}$, $R^{13-16}$ and R are as defined in the claims, or an acid addition salt thereof. The compounds of the invention posses the combined effect of serotonin reuptake inhibition and norepinephrine uptake inhibition.

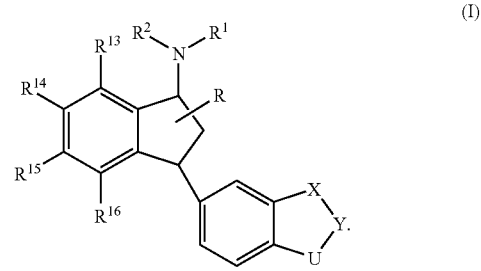

(I)

5 Claims, No Drawings

AMINOINDANE DERIVATIVES AS SEROTONIN AND NOREPINEPHRINE UPTAKE INHIBITORS

The invention provides novel aminoindane derivatives which are useful in the treatment of affective disorders, such as depression and anxiety disorders.

BACKGROUND OF THE INVENTION

The combined effect of serotonin reuptake inhibition and norepinephrine uptake inhibition on depression is explored in clinical studies of compounds such as Duloxetine (Wong DT: Duloxetine (LY-248686): an inhibitor of serotonin and noradrenaline uptake and an antidepressant drug candidate *Expert Opinion on Investigational Drugs* (1998) 7 10 1691-1699) and Venlafaxine (Khan-A; Fabre-LF; Rudolph-R: Venlafaxine in depressed outpatients *Psychopharmacology Bulletin* (1991) 27, 141-144).

The present invention provides novel compounds which posses the combined effect of serotonin reuptake inhibition and norepinephrine uptake inhibition for the treatment of affective disorders, such as depression, anxiety disorders including general anxiety disorder, social anxiety disorder, post traumatic stress disorder, obsessive compulsive disorder, panic disorder, panic attacks, specific phobias, social phobia and angoraphobia.

SUMMARY OF THE INVENTION

The present invention relates to compounds having the formula I

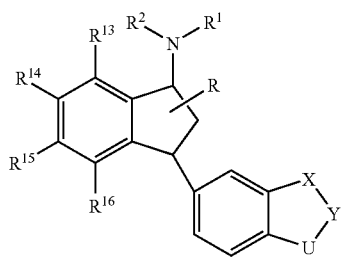

wherein
X is —O—, —S— or —$CR^4R^5$—;
Y is —$CR^6R^7$—, —$CR^6R^7$—$CR^8R^9$— or —$CR^6$=$CR^7$—;
or X and Y together form a group
—$CR^4$=$CR^5$—, or —$CR^4$=$CR^5$—$CR^6R^7$—; and
U is —O—, —S— or $CR^{10}R^{11}$; or
X is —O—, —S— or —$CR^4R^5$—; and
Y and U together form a group $CR^6$=$CR^7$—,
—$CR^6$=$CR^7$—$CR^{10}R^{11}$—,
or —$CR^6R^7$—$CR^{10}$=$CR^{11}$—;
or X and Y and U together form —$CR^4$=$CR^5$—$CR^6$=$CR^7$—;
$R^1$ and $R^2$ are independently selected from hydrogen, $C_{1-6}$-alkyl, $C_{2-6}$-alkenyl, $C_{2-6}$-alkynyl, $C_{3-8}$-cycloalkyl, or $R^1$ and $R^2$ together with the nitrogen, to which they are attached, form a 3-7-membered saturated ring optionally containing one further heteroatom;
$R^{13}$, $R^{14}$, $R^{15}$ and $R^{16}$ are each independently selected from hydrogen, halogen, cyano, nitro, $C_{1-6}$-alkyl, $C_{2-6}$-alkenyl, $C_{2-6}$-alkynyl, and $C_{3-8}$-cycloalkyl;
R is hydrogen, halogen, $C_{1-6}$-alkyl or cyano;

$R^4$, $R^5$, $R^6$, $R^7$, $R^8$, $R^9$, $R^{10}$ and $R^{11}$ are each independently selected from hydrogen a $C_{1-4}$-alkyl;
or an acid addition salt thereof;

The invention also provides a pharmaceutical composition comprising a compound of formula I or a pharmaceutically acceptable acid addition salt thereof and at least one pharmaceutically acceptable carrier or diluent.

The invention further provides the use of a compound of formula I or a pharmaceutically acceptable acid addition salt thereof for the preparation of a medicament for the treatment of affective disorders, such as depression and anxiety disorders including general anxiety disorder, social anxiety disorder, post traumatic stress disorder, obsessive compulsive disorder, panic disorder, panic attacks, specific phobias, social phobia and angoraphobia.

The invention also provides a method for the treatment of an affective disorder as mentioned above in a living animal body, including a human, comprising administering a therapeutically effective amount of a compound of formula I or a pharmaceutically acceptable acid addition salt thereof.

DETAILED DESCRIPTION OF THE INVENTION

According to one specific embodiment of the invention, X and U is selected from —O— and —S— and Y is —$CR^6R^7$—or —$CR^6R^7$—$CR^8R^9$—.

According to another specific embodiment of the invention, X and Y and U together form —$CR^4$=$CR^5$—$CR^6$=$CR^7$—.

Preferred compounds according to the invention are:
Trans-(3-Benzo[1,3]dioxol-5-yl-indan-1-yl)dimethylamine,
Cis-(3-Benzo[1,3]dioxol-5-yl-indan-1-yl)dimethylamine,
Trans-(3-Benzo[1,3]dioxol-5-yl-indan-1-yl)diethylamine,
Cis-(3-Benzo[1,3]dioxol-5-yl-indan-1-yl)diethylamine,
Trans-(3-Benzo[1,3]dioxol-5-yl-indan-1-yl)ethylamine,
Cis-(3-Benzo[1,3]dioxol-5-yl-indan-1-yl)ethylamine,
Trans-(3-Benzo[1,3]dioxol-5-yl-indan-1-yl)methylamine,
Cis-(3-Benzo[1,3]dioxol-5-yl-indan-1-yl)methylamine,
(+)-trans-(3-Benzo[1,3]dioxol-5-yl-indan-1-yl)dimethylamine,
(−)-trans-(3-Benzo[1,3]dioxol-5-yl-indan-1-yl)dimethylamine,
(+)-cis-(3-Benzo[1,3]dioxol-5-yl-indan-1-yl)dimethylamine,
(−)-cis-(3-Benzo[1,3]dioxol-5-yl-indan-1-yl)dimethylamine,
Trans-(3-Benzo[1,3]dioxol-5-yl-indan-1-yl)-ethyl-methylamine,
Cis-(3-Benzo[1,3]dioxol-5-yl-indan-1-yl)-ethyl-methylamine,
Cis-[3-(2,3-Dihydro-benzo[1,4]dioxin-6-yl)-indan-1-yl]-dimethyl-amine,
Trans-[3-(2,3-Dihydro-benzo[1,4]dioxin-6-yl)-indan-1-yl]-dimethyl-amine,
Cis-Dimethyl-(3-naphthalen-2-yl-indan-1-yl)-amine,
Trans-Dimethyl-(3-naphthalen-2-yl-indan-1-yl)-amine,
Cis-[3-(6-Chloro-benzo[1,3]dioxol-5-yl)-indan-1-yl]-dimethyl-amine,
Trans-[3-(6-Chloro-benzo[1,3]dioxol-5-yl)-indan-1-yl]-dimethyl-amine,
Cis-[3-(6-Chloro-benzo[1,3]dioxol-5-yl)-indan-1-yl]-methyl-amine,
Trans-[3-(6-Chloro-benzo[1,3]dioxol-5-yl)-indan-1-yl]-methyl-amine,
Cis-Enantiomer-1-(3-Benzo[1,3]dioxol-5-yl-indan-1-yl)-methyl-amine and Cis-Enantiomer-2-(3-Benzo[1,3]dioxol-5-yl-indan-1-yl)-methyl-amine or acid addition salts thereof.

As used herein halogen means fluoro, chloro, bromo or iodo.

The term $C_{1-6}$ alkyl refers to a branched or unbranched alkyl group having from one to six carbon atoms inclusive, such as methyl, ethyl, 1-propyl, 2-propyl, 1-butyl, 2-butyl, 2-methyl-2-propyl and 2-methyl-1-propyl.

Similarly, $C_{2-6}$ alkenyl and $C_{2-6}$ alkynyl, respectively, designate such groups having from two to six carbon atoms including one double bond and triple bond respectively, such as ethenyl, propenyl, butenyl, ethynyl, propynyl, and butynyl.

The term $C_{3-8}$ cycloalkyl designates a monocyclic or bicyclic carbocycle having three to eight C-atoms, such as cyclopropyl, cyclopentyl, cyclohexyl, cycloheptyl and cyclooctyl.

$R^1$ and $R^2$ may together with the nitrogen atom to which they are attached form a 3-7 membered ring optionally containing one further heteroatom, such as aziridinyl, azetidinyl, pyrrolidinyl, piperidinyl, morpholinyl, thiomorpholinyl and piperazinyl.

Exemplary of organic acid addition salts according to the invention are those formed with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic and theophylline acetic acids, as well as the 8-halotheophyllines, for example 8-bromotheophylline. Exemplary of inorganic acid addition salts according to the invention are those formed with hydrochloric, hydrobromic, sulfuric, sulfamic, phosphoric and nitric acids. The acid addition salts of the invention are preferably pharmaceutically acceptable salts formed with non-toxic acids.

The compounds of this invention may exist in unsolvated as well as in solvated forms with pharmaceutically acceptable solvents such as water, ethanol and the like. The solvated forms are considered equivalent to the unsolvated forms for the purposes of this invention.

Some of the compounds of the present invention contain chiral centres and such compounds exist in the form of isomers (e.g. enantiomers or diastereomers). The invention includes all such isomers and any mixtures thereof including racemic mixtures.

Racemic forms can be resolved into the optical antipodes by known methods, for example, by separation of diastereomeric salts thereof with an optically active acid, and liberating the optically active amine compound by treatment with a base. Racemic compounds of the present invention can thus be resolved into their optical antipodes, e.g., by fractional crystallisation of d- or l-(tartrates, mandelates or camphorsulphonate) salts for example. Another method for resolving racemates into the optical antipodes is based upon chromatography on an optically active matrix.

The compounds of the present invention may also be resolved by the formation of diastereomeric derivatives or by enzymatic resolvation.

Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981).

Optically active compounds can also be prepared from optically active starting materials.

The compounds of the invention may be prepared by:

1) Alkylating an amine of formula III with an alkylating reagent of formula II:

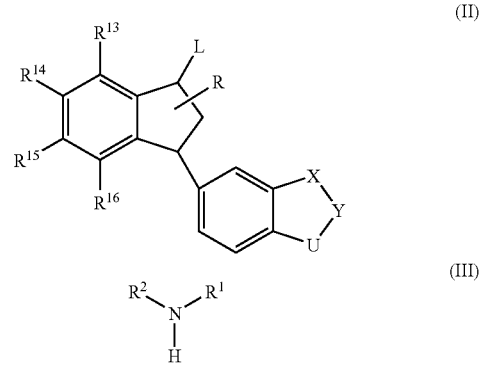

wherein R, $R^1$-$R^2$, $R^{13-16}$, X, Y and U are as previously defined, and L is a leaving group such as halogen, mesylate or tosylate;

2) Reductive alkylation of an indane ketone of formula IV with an amine of formula III:

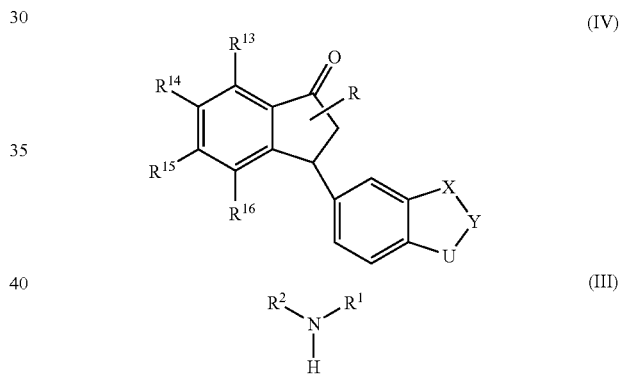

wherein R, $R^1$-$R^2$, $R^{13-16}$, X, Y and U are as previously defined;

3) Opening an epoxide of formula V with an amine of formula III:

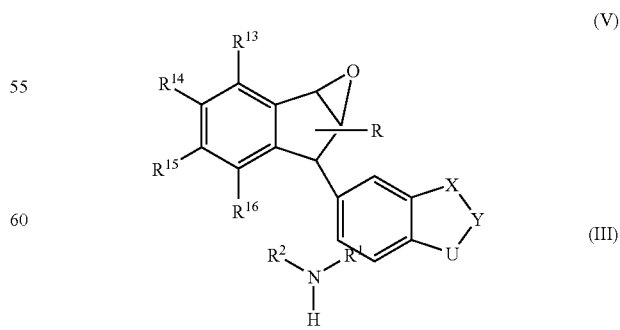

wherein R, $R^1$-$R^2$, $R^{13-16}$, X, Y and U are as previously defined.

The alkylation according to method 1) is conveniently performed in an organic solvent such as an alcohol or ketone with a suitable boiling point, preferably in the presence of an organic or inorganic base (potassium carbonate, diisopropylethylamine or triethylamine) at reflux temperature. Alternatively, the alkylation can be performed at a fixed temperature, which is different from the boiling point, in one of the above-k mentioned solvents or in dimethyl formamide (DMF), dimethylsulfoxide (DMSO) or N-methylpyrrolidin-2-one (NMP), preferably in the presence of a base such as those mentioned above. The alkylating derivatives of formula II have been described in the literature (e.g. Bøgesø, K. P. *J. Med. Chem.* 26, 1983, 935-947; Bøgesø, K. P. et al. *J. Med. Chem.* 28, 1985, 1817-1828: Sommer, M. B. et al. *J. Org. Chem.* 55, 1990, 4822-4827 and references cited therein) and the amines of formula m are commercially available.

The reductive alkylation according to method 2) is performed by standard literature methods. The reaction can be performed in one step under standard reductive amination conditions using e.g. sodium cyanoborohydride or in two steps, e.g. by condensation of amines of formula m with a reagent of formula IV followed by reduction of the resulting imine with sodium cyanoborohydride or sodium borohydride. The ketones of formula IV can be prepared as described in the literature (e.g. Bøgesø, K. P. *J. Med. Chem.* 26, 1983, 935-947; Bøgesø, K. P. et al. *J. Med. Chem.* 28, 1985, 1817-1828; Sommer, M. B. et al. *J. Org. Chem.* 55, 1990, 4822-4827 and references cited therein).

The epoxide opening according to method 3) is conveniently performed in an organic solvent such as a suitably boiling alcohol or ketone using an excess of an amine of formula III at reflux temperature.

Epoxides of formula IV can be prepared by methods described in the literature (e.g. Ghosh, A. K. et al. Synthesis 5; 1997; 541-544; Palmer, M. J. et al.; *J. Chem. Soc. Perkin Trans.* 1, 2002, 416-427).

The pharmaceutical formulations of the invention may be prepared by conventional methods in the art. For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilising the solution and filling it in suitable ampules or vials. Any suitable additive conventionally used in the art may be added, such as tonicity agents, preservatives, antioxidants, etc.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients or other additives normally used in the art may be used.

Conveniently, the compounds of the invention are administered in unit dosage form containing said compounds in an amount of about 0.01 to 100 mg. The total daily dose is usually in the range of about 0.05-500 mg, and most preferably about 0.1 to 50 mg of the active compound of the invention.

Experimental

The compounds of the invention exemplified in the following have been characterized using the following methods:

Melting points were determined on a Büchi B-540 apparatus and are uncorrected. Mass spectra were obtained on a Quattro MS-MS system from VG Biotech, Fisons Instruments. Analytical LC-MS data were obtained on a PE Sciex API 150EX instrument equipped with IonSpray source and Shiinadzu LC-8A/SLC-10A LC system. The LC conditions (50×4.6 mm YMC ODS-A with 5 μm particle size) were linear gradient elution with water/acetonitrile/trifluoroacetic acid (90:10:0.05) to water/acetonitrile/trifluoroacetic acid (10:90:0.03) in 7 min at 2 mL/min. Purity was determined by integration of the UV trace (254 nm). The retention times $R_t$ are expressed in minutes. Preparative LC-MS-separation was performed on the same instrument. The LC conditions (50×20 mm YMC ODS-A with 5 μm particle size) were linear gradient elution with water/acetonitrile/trifluoroacetic acid (80:20:0.05) to water/acetonitrile/trifluoroacetic acid (5:95:0.03) in 7 min at 22.7 mL/min. Fraction collection was performed by split-flow MS detection.

$^1$H NMR spectra were recorded at 250.13 MHz on a Bruker AC 250 or at 500.13 MHz on a Bruker DRX 500. Deuterated chloroform (99.8% D) or dimethylsulfoxide (99.9% D) were used as solvents. TMS was used as internal reference standard. Chemical shifts are expressed as ppm values. The following abbreviations are used for multiplicity of NMR signals: s=singlet, d=doublet, 1-triplet, q=quartet, qv=quintet, h=heptet, dd=double doublet, dt-double triplet, dq=double quartet, t-triplet of triplets, m=multiplet, b=broad. NMR signals corresponding to acidic protons are to some extent omitted. Content of water in crystalline compounds was determined by Karl Fischer titration. For column chromatography, silica gel of type Kieselgel 60, 40-60 mesh ASTM was used. For ion-exchange chromatography, the following material was used: SCX-columns (1 g) from Varian Mega Bond Elut®, Chrompack cat. No. 220776. Prior to use, the SCX-columns were pre-conditioned with 10% solution of acetic acid in methanol (3 mL).

EXAMPLES

Preparation of Intermediates

A. Alkylating Reagents

3-Amino-1-(benzo[1,3]dioxol-5-yl)-1-cyano-1H-indene-2-carboxylic acid methyl ester A mixture of 2-chlorobenzonitrile (12.3 g) and benzo[1,3]dioxol-5-yl-acetonitrile (10 g) in dimethylformamide (25 mL) was added with stirring and cooling in an ice bath to potassium tert-butoxide (20.1 g) dissolved in dimethylformamide (50 mL) at such a rate that the temperature did not exceed 25° C. After stirring for 0.5 h, methyl chloroacetate (11.1 g) was added in 10 min. After being stirred for 24 h at rt, the mixture was poured into a mixture of 0.1 M HCl (200 mL), heptane (30 mL) and toluene (15 mL). Stirring for 1 h, filtration and washing with water (2×50 mL), toluene (2×10 mL) and heptane (2×25 mL) afforded 79% of 3-Amino-1-benzo[1,3]dioxol-5-yl-1-cyano-1H-indene-2-carboxylic acid methyl ester.

3-(Benzo[1,3]dioxol-5-yl)-indan-1-one

A mixture of 3-amino-1-benzo[1,3]dioxol-5-yl-1-cyano-1H-indene-2-carboxylic acid methyl ester (10 g) and acetic acid, (30 mL) were heated to 100° C.; 60% aqueous sulfuric acid (20 mL) was added with stirring during 30 min. The mixture was heated to 110° C. for 6 h, cooled to rt, extracted with toluene (50+10 mL), washed with water (3×100 mL), extracted with 0.1 M aqueous sodium hydroxide (100+20 mL), acidified with concentrated hydrochloric acid, extracted with toluene (25+10 mL), and filtrated through activated carbon. Removal of the toluene gave 80% of 1-(benzo[1,3]dioxol-5-yl)-3-oxo-indan-1-carboxylic acid. The acid was subsequently decarboxylated by heating to 100° C. in N-methylpyrrolidone (15 mL) for 1 h. After cooling, the solution was poured into water (40 mL) with efficient stirring. Filtration, washing with water (5×20 mL), dissolution in ethyl acetate (40 mL), filtration through activated carbon and removal of the ethyl acetate gave 80% of 3-(benzo[1,3]dioxol-5-yl)-indan-1-one.

Cis-3-(benzo[1,3]dioxol-5-yl)-indan-1-ol

Sodium borohydride (1.5 g) was added in portions with stirring at 10-15° C. to a solution of 3-(benzo[1,3]dioxol-5-yl)-indan-1-one (10 g) in a mixture of ethanol (75 mL) and dimethoxyethane (75 mL). The mixture was stirred at rt for 1 h and then evaporated in vacuo. The resulting oil was treated with water and diethyl ether, and the organic phase was separated and washed with water and 0.1 N HCl, dried (MgSO4) and evaporated in vacuo to give cis-3-(benzo[1,3]dioxol-5-yl)-indan-1-ol as a brown oil (10 g).

5-(3-Chloro-indan-1-yl)-benzo[1,3]dioxole

Thionyl chloride (7 mL) was added with stirring and cooling at 15° C. to a solution of cis-3-(benzo[1,3]dioxol-5-yl)-indan-1-ol (10 g) in dichloromethane (300 mL). The mixture was stirred at rt for 40 min. The mixture was washed twice with water, dried (MgSO4) and evaporated in vacuo to give a quantitative yield of 5-(3-chloroindan-1-yl)benzo[1,3]dioxole as an oil, which was used in the next step without further purification.

Preparation of the Compounds of the Invention

Example 1 trans-(3-Benzo[1,3]dioxol-5-yl-indan-1-yl)dimethylamine(1) and cis-(3-Benzo[1,3]dioxol-5-yl-indan-1-yl)dimethylamine (2)

A mixture of 5-(3-chloroindan-1-yl)-benzo[1,3]dioxole (11 g) and 70 mL of 33% dimethylamine in ethanol was kept at 100° C. in a steel autoclave for 16 h. The mixture was cooled and evaporated in vacuo. The residue was dissolved in diethylether and washed with water and 2 N NaOH. The organic phase was dried (magnesium sulphate) evaporated in vacuo and the residue was purified by flash chromatography on silicagel using a gradient-eluent: 1) ethyl acetate/heptane (80:20) and 2) ethyl acetate/ethanol/triethylamine (90:10:4) to give the crude products as clear oils.

Trans-(3-Benzo[1,3]dioxol-5-yl-indan-1-yl)dimethylamine (1)

The slow-eluting compound is the trans isomer (3 g).
$^1$H NMR (CDCl$_3$): 1.95-2.05 (m, 1H); 2.30 (s, 6H); 2.60-2.70 (m, 1H); 4.40 (m, 2H); 5.90 (s, 2H); 6.55 (m, 1H); 6.65 (m, 1H), 6.70 (m, 1H), 6.95 (m, 1H), 7.25 (m, 1H), 7.45 (m, 1H). The compound could be converted to the fumarate salt from ethyl acetate/ethanol as a white crystalline compound.

Cis-(3-Benzo[1.3]dioxol-5-yl-indan-1-yl)dimethylamine (2)

The fast-eluting compound is the cis isomer (1 g).
$^1$H NMR (CDCl$_3$): 1.95-2.05 (m, 1H); 2.30 (s, 6H); 2.60-2.70 (m, 1H); 4.10 (m, 1H); 4.45 (m, 1H), 5.90 (s, 2H); 6.55 (m, 1H); 6.65 (m, 1H), 6.70 (m, 1H), 6.95 (m,1H) 7.25 (m, 1H), 7.45 (m, 1H). The compound could be converted to the fumarate salt from ethyl acetate/ethanol as a white crystalline compound.

The following compounds 3-14 were prepared analogously, HPLC-retention time and purity are described in table 1.:

Trans-(3-Benzo[1,3]dioxol-5-yl-indan-1-yl)diethylamine(3)
Cis-(3-Benzo[1,3]dioxol-5-yl-indan-1-yl)diethylamine(4)
Trans-(3-Benzo[1,3]dioxol-5-yl-indan-1-yl)ethylamine (5)
Cis-(3-Benzo[1,3]dioxol-5-yl-indan-1-yl)ethylamine (6)
Trans-(3-Benzo[1,3]dioxol-5-yl-indan-1-yl)methylamine (7)
Cis-(3-Benzo[1,3]dioxol-5-yl-indan-1-yl)methylamine (8)
Trans-(3-Benzo[1,3]dioxol-5-yl-indan-1-yl)-ethyl-methyl-amime (13)
Cis-(3-Benzo[1,3]dioxol-5-yl-indan-1-yl)-ethyl-methyl-amine (14)
Cis-[3-(2,3-Dihydro-benzo[1,4]dioxin-6-yl)-indan-1-yl]-dimethyl-amine (15)
Trans-[3-(2,3-Dihydro-benzo[1,4]dioxin-6-yl)-indan-1-yl]-dimethyl-amine (16)
Cis-Dimethyl-(3-naphthalen-2-yl-indan-1-yl)-amine (17)
Trans-Dimethyl-(3-naphthalen-2-yl-indan-1-yl)-amine (18)
Cis-[3-(6-Chloro-benzo[1,3]dioxol-5-yl)-indan-1-yl]-dimethyl-amine (19)
Trans-[3-(6-Chloro-benzo[1,3]dioxol-S-yl)-indan-1-yl]-dimethyl-amine (20)
Cis-[3-(6-Chloro-benzo[1,3]dioxol-5-yl)-indan-1-yl]-methyl-amine (21)
Trans-[3-(6-Chloro-benzo[1,3]dioxol-5-yl)-indan-1-yl]-methyl-amine (22)

TABLE 1

| Compound | Retention time (min) | Purity % (UV) | Purity % (ELSD) |
| --- | --- | --- | --- |
| 1 | 1.88 | 85.18 | 99.12 |
| 2 | 1.9 | 93.92 | 99.26 |
| 3 | 1.83 | 99.25 | 99.72 |
| 4 | 1.87 | 95.85 | 99.69 |
| 5 | 1.58 | 100 | 95.80 |
| 6 | 1.73 | 86.91 | 99.74 |
| 7 | 1.79 | 94.36 | 99.59 |
| 8 | 1.86 | 95.34 | 99.70 |
| 13 | 1.83 | 78.3 | 98.1 |
| 14 | 1.89 | 81.8 | 93.3 |
| 15 | 1.73 | 78.1 | 99.8 |
| 16 | 1.68 | 84.7 | 92.7 |
| 17 | 2.10 | 92.5 | 99.8 |
| 18 | 2.10 | 92.8 | 99.9 |
| 19 | 2.08 | 75.1 | 97.7 |
| 20 | 1.89 | 96.4 | 99.7 |
| 21 | 2.08 | 81.8 | 96.3 |
| 22 | 2.00 | 86.8 | 97.1 |
| 23 | 1.83 | 82.4 | 99.1 |
| 24 | 1.87 | 77.3 | 98.5 |

Example 2

(+)-trans-(3-Benzo[1.3]dioxol-5-yl-indan-1-yl)dimethylamine(9) and (−)-trans-(3-Benzo[1.3]dioxol-5-yl-indan-1-yl)dimethylamine(10)

Compound 1, trans-(3-Benzo[1,3]dioxol-5-yl-indan-1-yl) dimethylamine, was subjected to resolution by chiral HPLC using a Gilson SF3 supercritical fluid chromatography system equipped with chiralcelOD columns (4.6 mm×25 cm for analytical and 10 mm×25 cm for preparative runs). The particle size in the columns was 10 μm. A solution of compound 1, trans-(3-benzo[1,3]dioxol-5-yl-indan-1-yl) dimethylamine, (1 g) in methanol (1 nmL1) was injected in 40 μL portions on a preparative column. The column was eluted with carbondioxide—modifier (75:25). The modifier was 2-propanol with diethylamine(0.5%) and trifluoracetic acid (0.5%). The flow was 18.9 mL/min at 20 Mpa. Fraction collection was triggered by UV-detection (210 nM). The fractions containing the separate products were pooled and evaporated in vacuo which gave the enantiomers 9 and 10.

(+)-trans-(3-Benzo[1,3]dioxol-5-yl-indan-1-yl)dimethylamine (9): α=+14.0 (conc.=1% in Methanol)
(−)-trans-(3-Benzo[1,3]dioxol-5-yl-indan-1-yl)dimethylamine (10): α=−14.7 (conc.=1% in Methanol).

Example 3

(+)-cis-(3-Benzo[1.3]dioxol-5-yl-indan-1-yl)dimethylamine (11) and (−)-cis-(3-Benzo[1,3]dioxol-5-yl-indan-1-yl)dimethylamine(12)

Compound 2, cis-(3-benzo[1,3]dioxol-5-yl-indan-1-yl) dimethylamine, was subjected to resolution by chiral HPLC using a Gilson SF3 supercritical fluid chromatography system equipped with chiralcelOD columns (4.6 mm×25 cm for analytical and 10 mm×25 cm for preparative runs). The particle size in the columns was 10 μM. A solution of compound 2, cis-(3-benzo[1,3]dioxol-5-yl-indan-1-yl)dimethylamine, (1 g) in methanol (1 mL) was injected in 40 μL portions on a preparative column. The column was eluted with carbondioxide—modifier (75:25). The modifier was 2-propanol with diethylamine (0.5%) and trifluoracetic acid (0.5%). The flow was 18.9 mL/min at 20 Mpa. Fraction collection was triggered by UV-detection (210 nM). The fractions containing the separate products were pooled and evaporated in vacuo which gave the enantiomers 11 and 12.

(+)-cis-(3-Benzo[1,3]dioxol-5-yl-indan-1-yl)dimethylamine (11): α=+3.3 (conc.=1% in Methanol)
12. (−)-cis-(3-Benzo[1,3]dioxol-5-yl-indan-1-yl)dimethylamine(12): α=−4.4 (conc. =1% in Methanol).

The following Compounds were Prepared Analogously:
(+)-Cis-(3-Benzo[1,3]dioxol-5-yl-indan-1-yl)-methylamine(23)
(−)-Cis-(3-Benzo[1,3]dioxol-5-yl-indan-1-yl)-methylamine(24).

Pharmacological Testing

The compounds of the invention were tested in well-recognised and reliable tests. The tests were as follows:

Measurements of [³H]noradrenaline Uptake into Rat Cortical Synaptosomes.

Fresh cortex from male Wistar rats (125-225 g) are homogenized in 0.32 M sucrose supplemented with 1 mM nialamid with a glass/teflon homogenizer. The homogenate is centrifuged at 600×g for 10 min at 4° C. The pellet is discarded and the supernatant is centrifuged at 20.000×g for 55 min. The final pellet is homogenized (20 sec) in this assay buffer (6 mg original tissue/mL=4 mg/well). Test compounds (or buffer) and 10 nM [³H]-noradrenaline are added to deep 96 well plates and shaken briefly. Composition of assay buffer: 123 mM NaCl, 4.82 mM KCl, 0.973 mM CaCl$_2$, 1.12 mM MgSO$_4$, 12.66 mM Na$_2$BPO$_4$, 2.97 mM NaH$_2$PO$_4$, 0.162 mM EDTA, 10 mM glucose and 1 mM ascorbic acid. Buffer is oxygenated with 95% O$_2$/5% CO$_2$ for 10 min at 37° C. and pH is adjusted 7.4. The incubation is started by adding tissue to a final assay volume of 1 ml. After 15 min incubation with radioligand at 37° C., samples are filtered directly on Unifilter GF/C glass fiber filters (soaked for 1 hour in 0.1% polyethylenimine) under vacuum and immediately washed with 3×1 mL assay buffer. Non-specific uptake is determined using talsupram (10 μM final concentration). Duloxetine is included as reference in all experiments as dose-response curve.

Measurements of [³H]-5-HT Uptake into Rat Cortical Synaptosomes.

Whole brains from male Wistar rats (125-225 g), excluding cerebellum, are homogenized in 0.32 M sucrose supplemented with 1 mM nialamid with a glass/teflon homogenizer. The homogenate is centrifuged at 600×g for 10 min at 4° C. The pellet is discarded and the supernatant is centrifuged at 20.000×g for 55 min. The final pellet is homogenized (20 sec) in this assay buffer (0.5 mg original tissue/well). Test compounds (or buffer) and 10 nM [³H]-5-HT are added to 96 well plates and shaken briefly. Composition of assay buffer: 123 mM NaCl, 4.82 mM KCl, 0.973 mM CaCl$_2$, 1.12 mM MgSO$_4$, 12.66 mM Na$_2$BPO$_4$, 2.97 mM NaH$_2$PO$_4$, 0.162 mM EDTA, 10 mM glucose and 1 mM ascorbic acid. Buffer is oxygenated with 95% O$_2$/5% CO$_2$ for 10 min at 37° C. and pH is adjusted 7.4. The incubation is started by adding tissue to a final assay volume of 0.2 mL. After 15 min incubation with radioligand at 37° C., samples are filtered directly on Unifilter GF/C glass fiber filters (soaked for 1 hour in 0.1% polyethylenimine) under vacuum and immediately washed with 3×0.2 ml assay buffer. Non-specific uptake is determined using citalopram (10 μM final concentration). Citalopram is included as reference in all experiments as dose-response curve.

Results of the experiments shoved that the compounds of the invention showed that the compounds all inhibit the norepinephrine and serotonine uptake with IC$_{50}$ below 200 nM.

The invention claimed is:
1. An aminoindane compound having the formula I

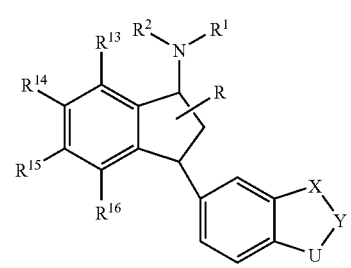

wherein
X is —O—, —S— or —CR$^4$R$^5$—;
Y is —CR$^6$R$^7$—, —CR$^6$R$^7$—CR$^8$R$^9$— or —CR$^6$=CR$^7$—; or X and Y together form a group —CR⁴=CR⁵—, or —CR⁴=CR⁵—CR⁶R⁷—, and U is —O—, —S— or CR¹⁰R¹¹; or X is —O—, —S— or —CR⁴R⁵—; and
Y and U together form a group CR⁶=CR⁷—, —CR⁶=CR⁷—CR¹⁰R¹¹—, or —CR⁶R⁷—CR¹⁰=CR¹¹—;

or X and Y and U together form —CR⁴=CR⁵—CR⁶=CR⁷—;

R¹ and R² are independently selected from hydrogen, $C_{1-6}$-alkyl, $C_{2-6}$-alkenyl, $C_{2-6}$-alkynyl, $C_{3-8}$-cycloalkyl, or R¹ and R² together with the nitrogen, to which they are attached, form a 3-7 membered ring optionally containing one further heteroatom;

R¹³, R¹⁴, R¹⁵ and R¹⁶ are each independently selected from hydrogen, halogen, cyano, nitro, $C_{1-6}$-alkyl, $C_{2-6}$-alkenyl, $C_{2-6}$-alkynyl, and $C_{3-8}$-cycloalkyl;

R is hydrogen, $C_{1-6}$-alkyl or cyano;

R⁴, R⁵, R⁶, R⁷, R⁸, R⁹, R¹⁰ and R¹¹ are each independently selected form hydrogen and $C_{1-4}$-alkyl;

or an acid addition salt thereof.

2. A compound according to claim 1 wherein X and U is selected from —O— and —S— and Y is —CR⁶R⁷— or —CR⁶R⁷—CR⁸R⁹—.

3. A compound according to claim 1 wherein X and Y and U together form —CR⁴=CR⁵—CR⁶=CR⁷—.

4. A compound selected from the group consisting of:
Trans-(3-Benzo[1,3]dioxol-5-yl-indan-1-yl)-dimethyl-amine,
Cis-(3-Benzo[1,3]dioxol-5-yl-indan-1-yl)-dimethyl-amine,
Trans-(3-Benzo[1,3]dioxol-5-yl-indan-1-yl)-diethyl-amine,
Cis-(3-Benzo[1,3]dioxol-5-yl-indan-1-yl)-diethyl-amine,
Trans-(3-Benzo[1,3]dioxol-5-yl-indan-1-yl)-ethyl-amine,
Cis-(3-Benzo[1,3]dioxol-5-yl-indan-1-yl)-ethyl-amine,
Trans-(3-Benzo[1,3]dioxol-5-yl-indan-1-yl)-methyl-amine,
Cis-(3-Benzo[1,3]dioxol-5-yl-indan-1-yl)-methyl-amine,
(+)-trans-(3-Benzo[1,3]dioxol-5-yl-indan-1-yl)-dimethyl-amine,
(−)-trans-(3-Benzo[1,3]dioxol-5-yl-indan-1-yl)-dimethyl-amine,
(+)-cis-(3-Benzo[1,3]dioxol-5-yl-indan-1-yl)-dimethyl-amine,
(−)-cis-(3-Benzo[1,3]dioxol-5-yl-indan-1-yl)-dimethyl-amine,
Trans-(3-Benzo[1,3]dioxol-5-yl-indan-1-yl)-ethyl-methyl-amine,
Cis-(3-Benzo[1,3]dioxol-5-yl-indan-1-yl)-ethyl-methyl-amine,
Cis-[3-(2,3-Dihydro-benzo[1,4]dioxin-6-yl)-indan-1-yl]-dimethyl-amine,
Trans-[3-(2,3-Dihydro-benzo[1,4]dioxin-6-yl)-indan-1-yl]-dimethyl-amine,
Cis-Dimethyl-(3-naphthalen-2-yl-indan-1-yl)-amine,
Trans-Dimethyl-(3-naphthalen-2-yl-indan-1-yl)-amine,
Cis-[3-(6-Chloro-benzo[1,3]dioxol-5-yl)-indan-1-yl]-dimethyl-amine,
Trans-[3-(6-Chloro-benzo[1,3]dioxol-5-yl)-indan-1-yl]-dimethyl-amine,
Cis-[3-(6-Chloro-benzo[1,3]dioxol-5-yl)-indan-1-yl]-methyl-amine,
Trans-[3-(6-Chloro-benzo[1,3]dioxol-5-yl)-indan-1-yl]-methyl-amine,
(+)-Cis-(3-Benzo[1,3]dioxol-5-yl-indan-1yl)-methyl-amine, and
(−)-Cis-(3-Benzol[1,3]dioxol-5yl-indan-1yl)-methyl-amine;

or an acid addition salt thereof.

5. A pharmaceutical composition comprising a compound according to any one of claims 1 to 4 or a pharmaceutically acceptable acid addition salt thereof and at least one pharmaceutically acceptable carrier or diluent.

* * * * *

UNITED STATES PATENT AND TRADEMARK OFFICE
CERTIFICATE OF CORRECTION

| | |
|---|---|
| PATENT NO. | : 7,351,734 B2 |
| APPLICATION NO. | : 10/496730 |
| DATED | : April 1, 2008 |
| INVENTOR(S) | : Klaus P. Bøgesø et al. |

It is certified that error appears in the above-identified patent and that said Letters Patent is hereby corrected as shown below:

Column 12, lines 28-29, "(+)-Cis-(3-Benzo[1,3]dioxol-5-yl-indan-lyl)-methyl-amine, and" should read -- (+)-Cis-(3-Benzo[1,3]dioxol-5-yl-indan-1-yl)-methyl-amine, and --

Column 12, lines 30-31, "(–)-Cis-(3-Benzol[1,3]dioxol-5yl-indan-lyl)-methyl-amine;" should read -- (–)-Cis-(3-Benzo[1.3]dioxol-5-yl-indan-1-yl)-methyl-amine; --

Signed and Sealed this

Twenty-second Day of July, 2008

JON W. DUDAS
*Director of the United States Patent and Trademark Office*